(12) United States Patent
Awaad et al.

(10) Patent No.: US 9,125,912 B1
(45) Date of Patent: Sep. 8, 2015

(54) METHOD OF TREATING ULCERATIVE COLITIS

(71) Applicant: KING SAUD UNIVERSITY, Riyadh (SA)

(72) Inventors: Amani Shafeek Awaad, Riyadh (SA); Nouf Al-Morai, Riyadh (SA); Reham M. El-Meligy, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/619,003

(22) Filed: Feb. 10, 2015

(51) Int. Cl.
*A61K 36/53* (2006.01)

(52) U.S. Cl.
CPC ...................... *A61K 36/53* (2013.01)

(58) Field of Classification Search
USPC .................................................. 424/725, 745
IPC ...................................................... A61K 36/53
See application file for complete search history.

(56) References Cited

U.S. PATENT DOCUMENTS

| | | | |
|---|---|---|---|
| 7,378,112 B2 | 5/2008 | Managoli | |
| 2004/0247700 A1* | 12/2004 | Babish et al. | 424/725 |
| 2005/0008710 A1* | 1/2005 | Subbiah | 424/725 |
| 2005/0013854 A1* | 1/2005 | Mannino et al. | 424/450 |
| 2005/0084547 A1* | 4/2005 | Subbiah | 424/740 |
| 2007/0160692 A1* | 7/2007 | Tripp et al. | 424/745 |
| 2009/0298941 A1* | 12/2009 | Gokaraju et al. | 514/557 |
| 2013/0203701 A1* | 8/2013 | Leighton | 514/62 |

FOREIGN PATENT DOCUMENTS

| | | | |
|---|---|---|---|
| BG | 106337 | * | 9/2003 |
| CN | 102631627 | * | 8/2012 |
| CN | 104138550 | * | 11/2014 |
| EP | 2599488 | * | 5/2013 |

OTHER PUBLICATIONS

Cristea et al. Farmacia. 1988. vol. 36, No. 1, pp. 51-54. DRUGU Abstract enclosed.*
Sarma et al. Pharmanest. 2011. vol. 2, No. 2-3, pp. 211-218.*
Singh, "Evaluation of Gastric Anti-Ulcer Activity of Fixed Oil of *Ocimum basilicum Linn*, and its Possible Mechanism of Action," *Indian Journal of Experimental Biology*, 1999, vol. 36, pp. 253-257.
Akhtar et al. "Antiulcerogenic Effects of *Ocimum basilicum* Extracts, Volatile Oils and Flavonoid Glycosides in Albino Rats," *Pharmaceutical Biology*, 1992, vol. 30, No. 2, pp. 97-104 (Abstract only).

\* cited by examiner

*Primary Examiner* — Chris R Tate
(74) *Attorney, Agent, or Firm* — Richard C. Litman

(57) ABSTRACT

The method of treating ulcerative colitis includes administering to a patient a therapeutically effective amount of an extract of *Ocimum americanum* L., *Ocimum basilicum*, or *Ocimum basilicum* var. *thyrsiflora*, to treat the ulcerative colitis in the patient. The extract can be a total alcohol extract, a total phenolic extract, or a volatile oil extract.

4 Claims, No Drawings

METHOD OF TREATING ULCERATIVE COLITIS

BACKGROUND OF THE INVENTION

1. Field of the Invention

The present invention relates to treating ulcerative colitis, and particularly to a method of treating ulcerative colitis using a plant extract.

2. Description of the Related Art

Ulcerative colitis (UC) is an inflammatory bowel disease that primarily affects the colonic mucosa and sub-mucosa. The most common symptoms of ulcerative colitis are ulcers and inflammation of the inner lining of the colon that lead to symptoms of bloody diarrhea, passage of pus, mucus, and abdominal cramping during bowel movements. Currently, there is no effective therapy to cure the disease. As such, treatment mainly depends on reduction of the symptoms. Most people with mild or moderate ulcerative colitis are treated with corticosteroids (dexamethasone, prednisone, methylprednisone, and hydrocortisone) to reduce inflammation and relieve symptoms. Other drugs typically used to treat symptoms include immunomodulators (azathioprine and 6-mercapto-purine) and aminosalicylates. Many of these drugs are associated with numerous side effects. Dexamethasone, for example, has many side effects on liver and kidney functions.

Thus, a method of treating ulcerative colitis solving the aforementioned problems is desired.

SUMMARY OF THE INVENTION

A method of treating ulcerative colitis can include administering to a patient a therapeutically effective amount of an extract of *Ocimum americanum*, *Ocimum basilicum*, or *Ocimum basilicum* var. *thyrsiflora*, to treat the ulcerative colitis in the patient. The extract can be a total alcohol extract, a total phenolic extract, or a volatile oil extract.

These and other features of the present invention will become readily apparent upon further review of the following specification and drawings.

DETAILED DESCRIPTION OF THE PREFERRED EMBODIMENTS

A method of treating ulcerative colitis can include administering to a patient a therapeutically effective amount of an extract of *Ocimum americanum* L., *Ocimum basilicum*, or *Ocimum basilicum* var. *thyrsiflora*, to treat ulcerative colitis in the patient. The extract can be a total alcohol extract, a total phenolic extract, or a volatile oil.

The present inventors have discovered that extracts of *Ocimum americanum*, *Ocimum basilicum* and *Ocimum basilicum* var. *thyrsiflora* each exhibit anti-ulcerative colitis activity. For example, when extracts of *Ocimum americanum*, *Ocimum basilicum* and *Ocimum basilicum* var. *thyrsiflora* were independently administered to rats five days prior to ulcer induction, all of the tested extracts showed anti-ulcerative activity. The alcohol extract achieved from about 65.92% to about 67.2% protection from control colitis. The total phenolics extract achieved from about 58.20% to about 60.11% protection from control colitis. The volatile oil extract achieved from about 5.95% to about 6.9% protection from control colitis. The percent protection from control colitis for dexamesthasone was about 71.54%. Thus, the alcohol extract of each plant was determined to be approximately as effective as dexamethasone (0.1 mg/kg). Unlike dexamethasone, however, the tested extracts did not exhibit side effects on liver or kidney functions. The tested extracts were determined to be safe for oral administration. For example, the alcohol extract was found to be safe in amounts as high as 4000 mg/kg.

Accordingly, extracts of *Ocimum americanum*, *Ocimum basilicum* and *Ocimum basilicum* var. *thyrsiflora* can be used to treat or prevent ulcerative colitis in a patient in need thereof. As used herein, the term "a patient in need thereof" refers to an individual suffering from ulcerative colitis, or an individual that elects to prevent ulcerative colitis.

A therapeutically effective amount of the extract or an amount effective to treat or prevent ulcerative colitis may be determined initially from in vivo assays described herein. For example, an effective amount of the total alcohol extract can be about 400 mg/kg. An effective amount of the total phenolic extract can be about 400 mg/kg. An effective amount of the volatile oil extract can be about 50 mg/kg.

The genus *Ocimum* includes important medicinal and aromatic herbs, undershrubs or shrubs. It belongs to the family Lamiaceae, subfamily Ocimoideae, and comprises more than 30 species distributed in tropical and subtropical regions of Asia, Africa, and Central and South America (Saha, 2013). Specific plants within the genus *Ocimum*, are referred to herein as *Ocimum* plants. *Ocimum* plants, as used herein, can include *Ocimum americanum*, *Ocimum basilicum*, and *Ocimum basilicum* var. *thyrsiflora*. *Ocimum americanum* is a native of tropical Africa. *Ocimum americanum*, also known as lime, hairy or hoary basil, is an annual herb with white or lavender flowers. It is used for medicinal purposes, as it exhibits antimicrobial and antioxidant activity. *Ocimum americanum* contains volatile oils, flavanoids, carbohydrates, phytosterols, tannins and fixed oils. *Ocimum basilicum*, or basil, is native to India, China, Southeast Asia, and New Guinea. *Ocimum basilicum* can have antioxidant, antiviral, and antimicrobial properties. *Ocimum basilicum*, collected from Ethiopia, was chemically examined by GC-MS. The main constituents of essential oil isolated by hydro distillation of the aerial parts was copaene (25.5%), p-menth-2-en-1-ol (7.7%), eugenylacetate (4.8%), bornyl acetate (4.0%), γ-himachalene (3.6%), rosifoliol (3.0%) and α-eubebene (2.5%). The essential oil of *O. basilicum* has shown significantly more antibacterial activity against gram positive (*Staphylococcus auerus*) than gram negative bacteria (*Escherichia coli*). *Ocimum basilicum* var. *thyrsiflora*, or Thai basil, is a type of sweet basil native to Southeast Asia.

To prepare the extract, raw materials can be collected from the whole of the *Ocimum* plants (i.e. stems, leaves, roots, flowers, etc.). Preferably, the raw materials are primarily or solely obtained from the leaves of the *Ocimum* plant. The raw materials collected from the *Ocimum* plant can be ground to small particle sizes. In addition, the raw materials can be dried to reduce water content. The raw materials can be air-dried, oven-dried, rotary evaporated under vacuum, lyophilized, or dried by any other suitable method known in the art. For example, the raw materials can be dried at room temperature.

The extract can be obtained by distilling the raw materials with a stripping agent. Suitable stripping agents include, but are not limited to the following: water; alcohols (such as methanol, ethanol, propanol, butanol and the like); glycols; ethers (such as diethyl ether, dipropyl ether, and the like); esters (such as butyl acetate, ethyl acetate, and the like); ketones (such as acetone, ethyl methyl ketone, and the like); dimethyl sulfoxide; acetonitrile; other organic solvents; and combinations thereof. For example, the volatile oil can be prepared by subjecting the leaves of the *Ocimum* plant to hydrodistillation. Further, water left after extraction of the volatile oils can be separately subjected to extraction with butanol to obtain the total phenolic extract. The total phenolic extract can include phenolic compounds and carbohydrates.

In other embodiments, the extract of the *Ocimum* plant can be an extract obtained by solvent extraction. For example, the raw materials can be washed and extracted. The raw materials can be whole or ground into small particle sizes, and then extracted using an organic solvent. Non-limiting examples of organic solvents include methanol, ethanol, isopropanol, dichloromethane, chloroform, hexane, xylene, and petroleum ether. For example, the alcohol extract can be prepared by extraction of the dried, powdered *Ocimum* plant using 90% ethanol. The collected extract can then be filtered to remove debris, and used directly, or concentrated, for example by distilling the solvent or by other conventional processing.

The present extract can be used as an active ingredient of a pharmaceutical composition for the prevention and/or treatment of ulcerative colitis. The composition of the present invention can be administered orally or parenterally (for example, application, intravenous, hypodermic, or peritoneal injection) but oral administration is preferred. For formulations for parenteral administration, powders, granules, tablets, capsules, sterilized suspensions, liquids, water-insoluble excipients, suspensions, emulsions, syrups, and suppositories can be used.

Solid formulations for oral administration can be powders, granules, tablets, capsules, soft capsules and pills. Liquid formulations for oral administrations can be suspensions, solutions, emulsions, syrups and aerosols, and the above-mentioned formulations can contain various excipients such as wetting agents, sweeteners, aromatics and preservatives in addition to generally used simple diluents such as water and liquid paraffin. The pharmaceutical composition can include, in addition to the above-mentioned effective ingredients, one or more pharmaceutically acceptable carriers for the administration. The pharmaceutically acceptable carrier can be selected or prepared by mixing more than one ingredients selected from the group consisting of saline, sterilized water, Ringer's solution, buffered saline, dextrose solution, maltodextrose solution, glycerol and ethanol. Other general additives such as anti-oxidative agent, buffer solution, bacteriostatic agent, etc., can be added. In order to prepare injectable solutions such as aqueous solution, suspension and emulsion, diluents, dispersing agents, surfactants, binders and lubricants can be added.

An effective dosage of the pharmaceutical composition of the present invention can be determined according to absorptiveness of the active ingredient, and age, gender and obesity of a patient by those in the art. The administration frequency can be once a day or a few times a day. The dosage cannot limit the scope of the present method by any means.

The following examples are provided by way of illustration.

Example 1

About 500 g of fresh leaves and flowers of *Ocimum americanum, Ocimum. Basilicum*, and *Ocimum basilicum* var. *thyrsiflora* were separately collected during the flowering stages in 2013, from Riyadh, Saudi Arabia. Plant samples were air-dried in shade, reduced to a fine powder, packed in tightly closed containers and stored for phytochemical and biological studies. For the essential oil extract, the plant was collected in the flowering stage and kept in the freezer until needed.

Example 2

Powdered samples from the aerial parts of *Ocimum americanum, Ocimum basilicum* and *Ocimum basilicum* var. *thyrsiflora* were subjected to phytochemical screening for their different constituents such as; carbohydrates and/or glycosides, flavonoides, tannins, sterols and/or triterpenes, proteins and/or amino acids, alkaloids and/or nitrogenous bases, saponins, anthraquinones, cardinolides and oxidase enzyme. The results of phytochemical screening are recorded in Table 1.

TABLE 1

Preliminary phytochemical screening of plants under investigation

| Test | Ocimum americanum | Ocimum basilicum | Ocimum basilicum var. thyrsiflora |
| --- | --- | --- | --- |
| Crystalline sublimate | − | − | − |
| Volatile oil | + | + | + |
| Tannins | + | + | + |
| Flavonoids | + | + | + |
| Alkaloids and/or nitrogenous bases | − | − | − |
| Cardinolides | − | − | − |
| Unsaturated sterols and/or triterpenoides | + | + | + |
| Saponins | − | − | − |
| Carbohydrates or glycosides | + | + | + |
| Anthraquinones | − | − | − |
| Proteins and/or amino acids | + | + | + |
| oxidase enzyme | − | − | − |

(−), absent; (+), present; (±), Traces.

Example 3

Essential oil (volatile oil) extracts and phenolic extracts were prepared as follows. For oil preparation; fresh leaves (500 g each) of *Ocimum americanum, Ocimum basilicum* and *Ocimum basilicum* var. *thyrsiflora* were subjected separately to hydrodistillation for 8 hours. The collected oil was dried over anhydrous sodium sulphate and subjected to GC/MS. The water left after extraction of the volatile oils was separately subjected to extraction with butanol (500 mL×4 times) to obtain other constituents (phenolic compounds and carbohydrates).

Example 4

Extraction and fractionations for the alcohol extract were conducted as follows. The air dried powdered samples of *Ocimum americanum, Ocimum. basilicum* and *Ocimum basilicum* var. *thyrsiflora* (1 kg) were extracted by percolation in 90% ethanol at room temperature for two days. The ethanol extracts were separately filtered and the residues were re-percolated four times for each plant. The total ethanol extracts were separately concentrated under reduced pressure at a temperature not exceeding 35° C.

Example 5

Swiss albino mice (26-30 g) of both sexes, and male Wistar rats (180-200 g) were purchased from the animal house of King Saud University (KSA). Animals were housed in standard polypropylene cages with wire mesh top and maintained under standard conditions (temperature 23±1.0° C., humidity 55±10%, 12 h light/12 h dark cycle). The animals were fed a standard pellet diet with water ad libitum and were allowed to adapt to the laboratory environment for one week before experimentation.

Example 6

Acute Toxicity Test

The oral median lethal dose ($LD_{50}$) of the alcohol extract of *Ocimum americanum, Ocimum. basilicum* and *Ocimum, basilicum* var. *thyrsiflora* was determined as described by Lorke (1983). Swiss albino mice in groups of six, received one of 500, 1000, 2000, or 4000 mg/kg doses of the tested extracts. Control animals received the vehicle and were kept under the same conditions. Signs of acute toxicity and number of deaths per dose within 24 hours were recorded.

The tested extracts were characterized by a low degree of toxicity. The results indicated that different doses of the alcohol extract of *Ocimum americanum, Ocimum. basilicum* and *Ocimum. basilicum* var. *thyrsiflora* up to 4000 mg/kg did not produce any symptoms of acute toxicity and none of the mice died during 24 h of observation. It was determined that oral $LD_{50}$ of the tested extract was higher than 4000 mg/kg and that the tested extracts are considered safe.

Example 7

Sub-Chronic Toxicity

Wistar rats were randomly divided into four groups each of 10 rats. The 1st group received the vehicle in a dose of 5 mL/kg and left as normal control. Rats of the 2nd, 3rd and 4th groups were separately administered with the alcohol extracts of *Ocimum americanum, Ocimum basilicum* and *Ocimum basilicum* var. *thyrsiflora* (400 mg/kg each). All extracts were administered orally daily for 14 consecutive days. Animals were maintained under identical conditions with food and water ad libitum for the entire period with close observation. At the end of the experimental period, blood samples (2 mL) were drawn by puncturing retro-orbital venous sinus of each rat (under ether anesthesia) and centrifuged at 10,000 rpm for 5 minutes. Sera were separated to be used for the biochemical estimations.

Liver functions were evaluated for the alcohol extracts of the three plants under investigation by measuring the serum activity of ALT and AST. Serum levels of total bilirubin, total proteins and albumin were also assayed. Serum concentrations of urea and creatinine were determined calorimetrically as measures of kidney functions.

The non-toxic nature of the *Ocimum americanum, Ocimum basilicum* and *Ocimum basilicum* var. *thyrsiflora* alcohol extracts in acute toxicity study is well supported by the results of sub-chronic toxicity study. Oral dosing of the tested extracts to rats (400 mg/kg) for 14 days did not show any significant effect on the levels of ALT, AST, total bilirubin, total proteins, albumin, urea and creatinine in their sera as compared to control, as shown in Table 2 below,

TABLE 2

Effect of the total alcohol extract of *Ocimum americanum, Ocimum basilicum*, and *Ocimum basilicum* var. *thyrsiflora* on liver and kidney functions.

| Parameter | Control | *Ocimum americanum* | *Ocimum basilicum* | *Ocimum basilicum* var. *thyrsiflora* |
|---|---|---|---|---|
| ALT (U/L) | 61.33 ± 2.48 | 65.30 ± 2.51 | 63.10 ± 2.01 | 65.30 ± 2.51 |
| AST (U/L) | 46.90 ± 2.25 | 50.40 ± 2.54 | 48.12 ± 2.24 | 50.40 ± 2.54 |
| Total bilirubin (mg/dL) | 1.70 ± 0.11 | 1.65 ± 0.10 | 1.67 ± 0.11 | 1.69 ± 0.14 |
| Total protein (g/dL) | 8.20 ± 0.09 | 8.30 ± 0.34 | 8.10 ± 0.14 | 8.21 ± 0.30 |
| Albumin (g/dL) | 3.7 ± 0.06 | 3.2 ± 0.11 | 3.3 ± 0.12 | 3.5 ± 0.21 |
| Urea (mg/dL) | 35.06 ± 2.35 | 37.33 ± 2.09 | 36.13 ± 2.19 | 34.35 ± 2.39 |
| Creatinine (mg/dL) | 0.43 ± 0.20 | 0.41 ± 0.25 | 0.42 ± 0.21 | 0.40 ± 0.35 |

Total alcohol extract of *Ocimum americanum, Ocimum basilicum* and *Ocimum basilicum* var. *thyrsiflora* (400 mg/kg) was administrated to rats for 14 days, n = 10, sera were collected and different enzymes were measured.

The serum transaminase level is most widely used as a measure of hepatic injury, due to its ease measurement and high degree of sensitivity. It is useful for the detection of early damage of hepatic tissue. Since the activity of ALT and AST are specific assayable liver enzymes, their normal levels in serum of rats treated for 14 days means that the alcohol extracts of *Ocimum americanum, Ocimum basilicum* and *Ocimum basilicum* var. *thyrsiflora* are not hepatotoxic.

Urea and creatinine are the most sensitive biochemical markers employed in the diagnosis of renal damage. In kidney damage, there will be retention of urea and creatinine in the blood, therefore marked increase in serum urea and creatinine are indications of functional damage to the kidney. By these indicators, the alcohol extracts of *Ocimum americanum, Ocimum. basilicum* and *Ocimum. basilicum* var. *thyrsiflora* are therefore, not nephrotoxic in rats.

Example 8

Effects on Ulcerative Colitis

The extracts (total alcohol extract, total phenolic contents and volatile oil) of the three plants under investigation were freshly suspended in distilled water just before administration by the aid of Tween 80.

The extracts of *Ocimum americanum, Ocimum basilicum* and *Ocimum basilicum* var. *thyrsiflora* were independently administered to rats five days prior to ulcer induction. In detail, twelve experimental groups, each of 6 Male Wistar rats were used. Rats of groups 1 and 2 received the vehicle (5 mL/kg) and served as normal control and control colitis groups. Dexamethasone (0.1 mg/kg) (a standard known drug) was administered to a third group, which served as a Reference group. Rats of groups 4-12 received the volatile oil extract, the total alcohol extract and the total phenolic extract of each of the three plants. Doses of 400 mg/kg of the total alcohol extract and the phenolic content were administered. Doses of 50 mg/kg of the volatile oil were administered. All medications were administered orally, once daily for 5 successive days and the last dose was administered 2 hours before colitis induction.

Animals were fasted overnight, with access to water ad libitum. Under ether anesthesia a solution of 2 mL (4%, v/v) acetic acid in saline was slowly infused into the colon through the polyethylene catheter 2 mm diameter that was inserted into the lumen of the colon via the anus to a distance of 8 cm. The model of acetic acid induced colitis shares many of the histologic features of ulcerative colitis in human beings including mucosal edema and submucosal ulceration.

In the sham group, an equivolume of normal saline was infused into the colon instead of acetic acid. Two days later, animals were sacrificed using ether anesthesia, colonic segments (8 cm in length and 3 cm proximal to the anus) were excised, opened along its mesenteric border, washed with saline, and were used for macroscopic scoring.

The colon specimens were weighted and wet weight/length ratio was calculated for all the rats. The specimens were examined under a dissecting microscope and the lesion scores were quantified by scoring system (0-5).

Ulcer area was measured using plane glass square. Each cell on the glass square was 1 $mm^2$ in area and the number of cells was counted and the ulcer area was determined for each colon.

and total phenolic content of *Ocimum americanum*, *Ocimum basilicum* and *Ocimum basilicum* var. *thyrsiflora* for 5 days prior to ulcer induction.

The highest activities were noticed with administration of alcohol extract of each plant; as their anti-ulcerative colitis activities were as effective as the standard dexamethasone (0.1 mg/kg). Administration of the alcohol extracts achieved a significant percentage of protection from control colitis (65.92% to 67.2%), while that achieved by dexamethasone was 71.54%. Total phenolic of each plant achieved results similar to that of the total alcohol extracts (58.20%-60.11% protection from colitis). Volatile oils of each plant achieved less significant results than the other extracts (5.95%-6.9% protection from colitis). The results are summarized in Table 3 below.

TABLE 3

Effects of all extract from *Ocimum americanum*, *Ocimum. Basilicum* and *Ocimum. basilicum* var. *thyrsiflora* on the macroscopic parameters of ulcerative colitis induced by acetic acid in rats.

| Groups | Dose | Lesion score (0-5) | Ulcer area ($mm^2$) | Ulcer index | Wet W/L (g/cm) | % Protection from control colitis |
|---|---|---|---|---|---|---|
| Normal control | 5 mL/kg | 0.00 ± 0.00 | 0.00 ± 0.00 | 0.00 ± 0.00 | 0.38 ± 0.05 | — |
| Control colitis | 5 mL/kg | 4.00 ± 0.89 | 58.20 ± 1.21 | 62.20 ± 1.86 | 0.96 ± 0.09 | — |
| Dexamethasone | 0.1 mg/kg | 1.50* ± 0.55 | 16.20* ± 1.17 | 17.70* ± 1.03 | 0.51* ± 0.09 | 71.54 |
| Alcohol extract of *Ocimum americanum* | 400 mg/kg | 1.80* ± 0.24 | 19.4* ± 0.27 | 21.20* ± 0.39 | 0.55* ± 0.04 | 65.92 |
| Total phenolic content *Ocimum americanum* | 400 mg/kg | 2.00* ± 0.15 | 24.00* ± 0.27 | 26.00* ± 0.34 | 0.48* ± 0.05 | 58.20 |
| Volatile oil of *Ocimum americanum* | 50 mg/kg | 3.50 ± 0.23 | 55.00 ± 0.30 | 58.50 ± 0.43 | 0.86 ± 0.05 | 5.95 |
| Alcohol extract of *Ocimum. Basilicum* | 400 mg/kg | 1.60* ± 0.16 | 17.2* ± 0.17 | 19.42* ± 0.29 | 0.53* ± 0.02 | 67.20 |
| Total phenolic content *Ocimum. Basilicum* | 400 mg/kg | 1.70* ± 0.11 | 22.00* ± 0.07 | 23.01* ± 0.12 | 0.46* ± 0.11 | 60.11 |
| Volatile oil of *Ocimum. Basilicum* | 50 mg/kg | 2.92 ± 0.23 | 51.97 ± 0.20 | 52.10 ± 0.40 | 0.83 ± 0.06 | 6.90 |
| Alcohol extract of *Ocimum. basilicum* var. *thyrsiflora* | 400 mg/kg | 1.70* ± 0.14 | 18.45* ± 0.20 | 20.22* ± 0.15 | 0.54* ± 0.00 | 66.52 |
| Total phenolic content of *Ocimum. basilicum* var. *thyrsiflora* | 400 mg/kg | 1.90* ± 0.11 | 23.01* ± 0.17 | 24.80* ± 0.22 | 0.50* ± 0.01 | 59.15 |
| Volatile oil of *Ocimum. basilicum* var. *thyrsiflora* | 50 mg/kg | 3.01 ± 0.21 | 53.02 ± 0.40 | 55.60 ± 0.11 | 0.84 ± 0.12 | 6.27 | n = 6
*Significantly different from control colitis at $p < 0.05$.

Ulcer index (UI) was measured by summing the lesion score and the ulcer area for each colon specimen. The curative ratio was determined according to the formula: Curative ratio=Control UI–Test UI/Control UI×100.

Data were expressed as mean±S. D. Statistical analysis was done by using SPSS 14. Statistical significance of differences between two means was assessed by unpaired Student's 't' test. Differences at p<0.05, 0.01, and 0.001 were considered statistically significant.

In rats of the sham group, no abnormal changes were observed suggesting that the handling procedure had no interference with the experimental outputs. Macroscopic damage parameters of the colon of control colitis rats, two days after rectal infusion of acetic acid revealed dark brown lesions, mucosal hyperemia, edema, erosion, and ulceration. Control colitis rats showed lesion score, ulcer area and ulcer index values of 4.00±0.89, 58.20±1.21, 62.20±1.86 and 0.96±0.09, respectively. The inflammatory changes of the intestinal tract were associated with a significant increase of wet weight/length of the colon specimens as an indicator of inflammation. These inflammatory indices were significantly improved by oral dosing of dexamethasone, volatile oils, alcohol extract It is to be understood that the present invention is not limited to the embodiments described above, but encompasses any and all embodiments within the scope of the following claims.

We claim:

1. A method of treating ulcerative colitis in a patient in need thereof, comprising:
   administering a therapeutically effective amount of an extract of *Ocimum americanum* to the patient,
   wherein the extract is selected from the group consisting of an alcoholic extract, a phenolic extract, and a volatile oil extract.

2. The method of treating ulcerative colitis according to claim 1, wherein a therapeutically effective amount of the alcoholic extract is about 400 mg/kg.

3. The method of treating ulcerative colitis according to claim 1, wherein a therapeutically effective amount of the phenolic extract is about 400 mg/kg.

4. The method of treating ulcerative colitis according to claim 1, wherein a therapeutically effective amount of the volatile oil extract is about 50 mg/kg.

* * * * *